(12) United States Patent
Tonn et al.

(10) Patent No.: US 11,272,975 B2
(45) Date of Patent: Mar. 15, 2022

(54) SYSTEMS AND METHODS FOR CONTROLLED ELECTROSURGICAL DISSECTION

(71) Applicant: COVIDIEN LP, Mansfield, MA (US)

(72) Inventors: Donald L. Tonn, Superior, CO (US); James E. Dunning, Lafayette, CO (US); William D. Faulkner, Boulder, CO (US); Jennifer R. McHenry, Denver, CO (US); Devon E. Scott-Drechsel, Superior, CO (US); Eric M. Westra, Loveland, CO (US)

(73) Assignee: COVIDIEN LP, Mansfield, MA (US)

( * ) Notice: Subject to any disclaimer, the term of this patent is extended or adjusted under 35 U.S.C. 154(b) by 688 days.

(21) Appl. No.: 16/121,843

(22) Filed: Sep. 5, 2018

(65) Prior Publication Data
US 2019/0090930 A1 Mar. 28, 2019

Related U.S. Application Data

(60) Provisional application No. 62/562,078, filed on Sep. 22, 2017, provisional application No. 62/562,012, (Continued)

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1233* (2013.01); *A61B 18/1445* (2013.01);
(Continued)

(58) Field of Classification Search
CPC ............ A61B 18/1206; A61B 18/1233; A61B 18/1445; A61B 2018/1462;
(Continued)

(56) References Cited

U.S. PATENT DOCUMENTS 5,472,443 A 12/1995 Cordis et al.
6,080,149 A 6/2000 Huang et al.
(Continued)

FOREIGN PATENT DOCUMENTS

CN 106163437 A 11/2016
DE 179607 C 3/1905
(Continued)

OTHER PUBLICATIONS

Extended European Search Report issued in corresponding EP Application No. 18195881.0 dated Dec. 10, 2018, 7 pages.
(Continued)

*Primary Examiner* — Linda C Dvorak
*Assistant Examiner* — Nils A Potter

(57) ABSTRACT

The disclosed systems and methods relate to controlling the application of electrosurgical energy by an electrosurgical instrument. An electrosurgical generator in accordance with the present disclosure includes a processor and a memory storing instructions executable by the processor. The instructions when executed, cause the generator to receive signals from the instrument over time relating to whether tissue is grasped by the instrument, receive an indication to provide an indicated treatment power to the instrument where the indicated treatment power is set by a user, determine based on the signals that tissue is currently grasped and that, for at least a predetermined length of time prior, no tissue had been grasped, and based on the determination, provide a treatment power surge to the instrument for a surge time period. After the surge time period, the generator provides the indicated treatment power to the instrument.

15 Claims, 4 Drawing Sheets

Related U.S. Application Data filed on Sep. 22, 2017, provisional application No. 62/562,110, filed on Sep. 22, 2017.

(51) Int. Cl.
*A61B 18/00* (2006.01)
*A61B 90/00* (2016.01)

(52) U.S. Cl.
CPC .................. *A61B 2018/0063* (2013.01); *A61B 2018/00589* (2013.01); *A61B 2018/00601* (2013.01); *A61B 2018/00607* (2013.01); *A61B 2018/00642* (2013.01); *A61B 2018/00648* (2013.01); *A61B 2018/00702* (2013.01); *A61B 2018/00761* (2013.01); *A61B 2018/00767* (2013.01); *A61B 2018/00827* (2013.01); *A61B 2018/00875* (2013.01); *A61B 2018/00886* (2013.01); *A61B 2018/00892* (2013.01); *A61B 2018/00904* (2013.01); *A61B 2018/126* (2013.01); *A61B 2018/1253* (2013.01); *A61B 2018/1266* (2013.01); *A61B 2018/1462* (2013.01); *A61B 2090/065* (2016.02)

(58) Field of Classification Search
CPC ........... A61B 2018/00589; A61B 2018/00886; A61B 2090/065; A61B 2018/00642; A61B 2018/00761; A61B 2018/00904; A61B 2018/00648; A61B 2018/00892; A61B 2018/00767; A61B 2018/1253; A61B 2018/126; A61B 2018/1266; A61B 2018/00601; A61B 2018/00607; A61B 2018/0063; A61B 2018/00702; A61B 2018/00827; A61B 2018/00875; A61B 18/12; A61B 18/1442; A61B 2018/1467
USPC .......................................................... 606/34
See application file for complete search history.

(56) References Cited

U.S. PATENT DOCUMENTS

| | | | |
|---|---|---|---|
| 6,228,081 B1 * | 5/2001 | Goble | A61B 18/1206 606/34 |
| 6,468,270 B1 | 10/2002 | Hovda et al. | |
| 6,837,888 B2 | 1/2005 | Ciarrocca et al. | |
| 6,942,660 B2 | 9/2005 | Pantera et al. | |
| 6,974,453 B2 | 12/2005 | Woloszko et al. | |
| D574,323 S | 8/2008 | Waaler | |
| 8,095,212 B2 | 1/2012 | Sato | |
| 9,270,202 B2 | 2/2016 | Johnson et al. | |
| 9,283,028 B2 | 3/2016 | Johnson | |
| 9,737,355 B2 | 8/2017 | Yates et al. | |
| 2002/0029036 A1 | 3/2002 | Goble et al. | |
| 2002/0165531 A1 | 11/2002 | Goble | |
| 2004/0167508 A1 | 8/2004 | Wham et al. | |
| 2005/0119646 A1 | 6/2005 | Scholl et al. | |
| 2005/0203504 A1 | 9/2005 | Wham et al. | |
| 2006/0217707 A1 | 9/2006 | Daniel et al. | |
| 2007/0173811 A1 | 7/2007 | Couture et al. | |
| 2007/0265616 A1 | 11/2007 | Couture et al. | |
| 2008/0221565 A1 | 9/2008 | Eder et al. | |
| 2008/0287944 A1 | 11/2008 | Pearson et al. | |
| 2009/0240244 A1 | 9/2009 | Malis et al. | |
| 2009/0254077 A1 | 10/2009 | Craig | |
| 2010/0106158 A1 | 4/2010 | Sato | |
| 2011/0015631 A1 * | 1/2011 | Wiener | A61B 18/1445 606/42 |
| 2011/0028963 A1 | 2/2011 | Gilbert | |
| 2011/0037484 A1 | 2/2011 | Gilbert | |
| 2011/0038056 A1 | 2/2011 | Nakamura | |
| 2011/0106141 A1 | 5/2011 | Nakamura | |
| 2011/0208183 A1 | 8/2011 | Stocked | |
| 2012/0078139 A1 | 3/2012 | Aldridge et al. | |
| 2012/0179154 A1 | 7/2012 | Goldberg et al. | |
| 2014/0100559 A1 | 4/2014 | Wham et al. | |
| 2014/0232463 A1 | 8/2014 | Gilbert | |
| 2014/0243815 A1 | 8/2014 | Kerr | |
| 2014/0253140 A1 | 9/2014 | Gilbert | |
| 2014/0257270 A1 | 9/2014 | Behnke | |
| 2014/0258800 A1 | 9/2014 | Gilbert | |
| 2014/0276659 A1 | 9/2014 | Juergens et al. | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |
| 2014/0358138 A1 | 12/2014 | Mattmiller et al. | |
| 2014/0376269 A1 | 12/2014 | Johnson et al. | |
| 2015/0025521 A1 | 1/2015 | Friedrichs et al. | |
| 2015/0025523 A1 | 1/2015 | Friedrichs et al. | |
| 2015/0032096 A1 | 1/2015 | Johnson | |
| 2015/0032098 A1 | 1/2015 | Larson et al. | |
| 2015/0032099 A1 | 1/2015 | Larson et al. | |
| 2015/0032100 A1 | 1/2015 | Coulson et al. | |
| 2015/0088116 A1 | 3/2015 | Wham | |
| 2015/0088117 A1 | 3/2015 | Gilbert et al. | |
| 2015/0088118 A1 | 3/2015 | Gilbert et al. | |
| 2015/0088124 A1 | 3/2015 | Wham | |
| 2015/0088125 A1 | 3/2015 | Wham | |
| 2015/0119871 A1 | 4/2015 | Johnson et al. | |
| 2016/0270840 A1 * | 9/2016 | Yates | A61B 18/1445 |
| 2017/0181701 A1 * | 6/2017 | Fehrenbacher | A61B 17/29 |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 102008058737 A1 | 4/2010 |
| EP | 0246350 A1 | 11/1987 |
| EP | 0267403 A2 | 5/1988 |
| EP | 0296777 A2 | 12/1988 |
| EP | 0310431 A2 | 4/1989 |
| EP | 0325456 A2 | 7/1989 |
| EP | 0336742 A2 | 10/1989 |
| EP | 0390937 A1 | 10/1990 |
| EP | 0556705 A1 | 8/1993 |
| EP | 0608609 A2 | 8/1994 |
| EP | 0836868 A2 | 4/1998 |
| EP | 0880220 A2 | 11/1998 |
| EP | 0882955 A1 | 12/1998 |
| EP | 1051948 A2 | 11/2000 |
| EP | 1366724 A1 | 12/2003 |
| EP | 1776929 A1 | 4/2007 |
| EP | 2111812 A2 | 10/2009 |
| EP | 2649956 A1 | 10/2013 |
| FR | 1275415 A | 11/1961 |
| FR | 1347865 A | 1/1964 |
| FR | 2313708 A1 | 12/1976 |
| FR | 2364461 A1 | 4/1978 |

(56) References Cited

FOREIGN PATENT DOCUMENTS

| FR | 2502935 A1 | 10/1982 |
|---|---|---|
| FR | 2517953 A1 | 6/1983 |
| FR | 2573301 A1 | 5/1986 |
| JP | 63005876 | 1/1988 |
| JP | 2002065690 A | 3/2002 |
| JP | 2005000224 A | 1/2005 |
| JP | 2005185657 A | 7/2005 |
| JP | 2006506173 A | 2/2006 |
| SU | 166452 | 11/1964 |
| SU | 727201 A2 | 4/1980 |
| WO | 0211634 A1 | 2/2002 |
| WO | 0245589 A2 | 6/2002 |
| WO | 03090635 A1 | 11/2003 |
| WO | 2006/050888 A1 | 5/2006 |
| WO | 2008053532 A1 | 5/2008 |
| WO | 2008071914 A2 | 6/2008 |

OTHER PUBLICATIONS

Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'", Neurosurgical Review 7:2-3 (1984) pp. 187-190.
Sugita et al., "Bipolar Coagulator with Automatic Thermocontrol", J. Neurosurg., vol. 41, Dec. 1944, pp. 777-779.
Prutchi et al. "Design and Development of Medical Electronic Instrumentation", John Wiley & Sons, Inc. 2005.
Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.
Muller et al. "Extended Left Hemicolectomy Using the LigaSure Vessel Sealing System", Innovations That Work Company Newsletter; Sep. 1999.
"Electrosurgical Unit Analyzer ESU-2400 Series User Manual" Apr. 1, 2002; Retrieved from Internet: <URL:http://www.bcgroupintl.com/ESU_2400/Updates/ESU-2400_UM_Rev04.pdf>, pp. 6, 11, 73.
Ogden Goertzel Alternative to the Fourier Transform: Jun. 1993 pp. 485-487, Electronics World; Reed Business Publishing, Sutton, Surrey, BG vol. 99, No. 9. 1687.
Hadley I C D et al., "Inexpensive Digital Thermometer for Measurements on Semiconductors", International Journal of Electronics; Taylor and Francis. Ltd ; London, GB; vol. 70, No. 6 Jun. 1, 1991; pp. 1155-1162.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence" Am. J. Ml, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International Conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
Chinese First Office Action dated Oct. 12, 2020 corresponding to counterpart Patent Application CN 201811104491.9.
Japanese Office Action dated Jul. 9, 2019 corresponding to counterpart Patent Application No. JP 2018-177150.
Chinese First Office Action dated Apr. 27, 2021 corresponding to counterpart Patent Application CN 201811104491.9.

* cited by examiner

SYSTEMS AND METHODS FOR CONTROLLED ELECTROSURGICAL DISSECTION

CROSS-REFERENCE TO RELATED APPLICATIONS

The present application claims priority to U.S. Provisional Application No. 62/562,012, filed on Sep. 22, 2017, U.S. Provisional Application No. 62/562,078, filed on Sep. 22, 2017, and U.S. Provisional Application No. 62/562,110, filed on Sep. 22, 2017. The entire contents of each of the foregoing applications are hereby incorporated by reference.

BACKGROUND

1. Technical Field

The present disclosure generally relates to electrosurgical generators. More particularly, the present disclosure relates to systems and methods for providing, controlling, and applying electrosurgical energy for dissection of tissue.

2. Background of Related Art

An electrosurgical generator is used in surgical procedures to provide electrical energy for treating the tissue of a patient. When bipolar forceps or another electrosurgical instrument is connected to the generator, the instrument can be used for cutting, coagulation, or sealing the tissue of a patient with high frequency electrical energy. During operation, electrical current from the generator flows between an active electrode and a return electrode of the instrument by passing through tissue and bodily fluids of a patient.

The electrical energy provided by the electrosurgical generator has different waveforms shaped to enhance its ability to cut, coagulate, or seal tissue. Different waveforms correspond to different modes of operating the generator, and each mode provides the surgeon various operating advantages. A surgeon can select and change various modes of operation as the surgical procedure progresses.

In the various modes, it is important to apply the appropriate amount of energy for the electrosurgical procedure. For example, applying too much energy may result in undesirable destruction of tissue. Applying too little energy may inhibit the surgical procedure. Therefore, it is desirable to control the amount of energy provided by the electrosurgical generator for the surgical procedure being performed and for the operating conditions that are encountered. Accordingly, there is continued interest in developing and improving the control of electrical energy provided by an electrosurgical generator.

SUMMARY

The present disclosure relates to systems and methods for providing, controlling, and applying electrosurgical energy for dissection of tissue. As will be described herein in more detail, when tissue is grasped by an electrosurgical instrument and, for a predetermined length of time prior, no tissue had been grasped, a controlled power surge can be provided to the instrument for use in treating tissue.

In accordance with aspects of the present disclosure, the present disclosure includes an electrosurgical generator for providing electrical treatment energy to an instrument. The generator includes a processor and a memory storing instructions which are executable by the processor. When the instructions are executed, they cause the generator to receive signals from the instrument over time relating to whether tissue is grasped by the instrument, receive an indication to provide an indicated treatment power to the instrument, where the indicated treatment power is set by a user, determine based on the signals that tissue is grasped and that no tissue had been grasped for at least a predetermined length of time, and based on the determination, provide a treatment power surge to the instrument for a surge time period, where the treatment power surge is greater than the indicated treatment power. After the surge time period, the generator provides the indicated treatment power to the instrument.

In various embodiments, the treatment power surge peaks at one and half to four times the indicated treatment power. In various embodiments, the indicated treatment power set by the user is set for a tissue dissection mode of the generator, and the instrument is a bipolar forceps that utilizes the indicated treatment power to dissect tissue.

In various embodiments, the signals received from the instrument over time include return current from the instrument to the generator, and the generator includes a sensor configured to measure the return current.

In various embodiments, the memory includes further instructions which, when executed by the processor, cause the generator to determine, based on the return current, a load impedance of a load of the instrument. In various embodiments, in determining that tissue is grasped, the memory includes further instructions which, when executed by the processor, cause the generator to determine that tissue is grasped based on the load impedance being lower than a load impedance threshold. In various embodiments, in determining that, for at least a predetermined length of time, no tissue had been grasped, the memory includes further instructions which, when executed by the processor, cause the generator to determine that no tissue had been grasped based on the load impedance being higher than a load impedance threshold for the predetermined length of time.

In various embodiments, the signals received from the instrument over time relating to whether tissue is grasped by the instrument include one or more of: signals of a pressure sensor of the instrument indicative of whether tissue is in contact with the pressure sensor, signals of a light sensor of the instrument indicative of whether tissue is occluding light from reaching the light sensor, signals of a manual switch of the instrument indicative of whether a user has operated the switch to indicate that tissue is grasped, or voltage signals for determining a crest factor for voltage provided by the generator.

In accordance with aspects of the present disclosure, the present disclosure includes a method in an electrosurgical generator for providing electrical treatment energy to an instrument. The method includes receiving signals from the instrument over time relating to whether tissue is grasped by the instrument, receiving an indication to provide an indicated treatment power to the instrument, where the indicated treatment power is set by a user, determining based on the signals that tissue is grasped and that no tissue had been grasped for at least a predetermined length of time, and providing, based on the determining, a treatment power surge to the instrument for a surge time period, where the treatment power surge is greater than the indicated treatment power. After the surge time period, the method includes providing the indicated treatment power to the instrument.

In various embodiments, the treatment power surge peaks at one and half to four times the indicated treatment power. In various embodiments, the indicated treatment power set by the user is set for a tissue dissection mode of the generator, and the instrument is a bipolar forceps that utilizes the indicated treatment power to dissect tissue.

In various embodiments, receiving signals from the instrument over time includes receiving a return current from the instrument to the generator, and the method further includes measuring the return current.

In various embodiments, the method further includes determining, based on the return current, a load impedance of a load of the instrument. In various embodiments, determining that tissue is grasped includes determining that tissue is grasped based on the load impedance being lower than a load impedance threshold. In various embodiments, determining that no tissue had been grasped for at least a predetermined length of time includes determining that no tissue had been grasped based on the load impedance being higher than a load impedance threshold for the predetermined length of time.

In various embodiments, the signals received from the instrument over time relating to whether tissue is grasped by the instrument include one or more of: signals of a pressure sensor of the instrument indicative of whether tissue is in contact with the pressure sensor, signals of a light sensor of the instrument indicative of whether tissue is occluding light from reaching the light sensor, signals of a manual switch of the instrument indicative of whether a user has operated the switch to indicate that tissue is grasped, or voltage signals for determining a crest factor for voltage provided by the generator.

In accordance with aspects of the present disclosure, the present disclosure includes a system for treating tissue. The system includes an electrosurgical instrument configured to receive electrical treatment energy and to treat tissue and an electrosurgical generator. The electrosurgical generator includes a processor and a memory storing instructions executable by the processor. When the instructions are executed, they cause the generator to receive signals from the electrosurgical instrument over time relating to whether tissue is grasped by the electrosurgical instrument, receive an indication to provide an indicated treatment power to the electrosurgical instrument where the indicated treatment power is set by a user, determine based on the signals that tissue is grasped and that no tissue had been grasped for at least a predetermined length of time, and, based on the determination, provide a treatment power surge to the electrosurgical instrument for a surge time period, where the treatment power surge is greater than the indicated treatment power. After the surge time period, the generator provides the indicated treatment power to the electrosurgical instrument.

BRIEF DESCRIPTION OF THE DRAWINGS

Various embodiments of the present disclosure are described with reference to the accompanying drawings wherein.

DETAILED DESCRIPTION

The present disclosure relates to systems and methods for providing, controlling, and applying electrosurgical energy for dissection of tissue. As will be described herein in more detail, in one aspect of the present disclosure, when tissue is grasped by an electrosurgical instrument and, for a predetermined length of time prior, after no tissue had been grasped, a controlled power surge can be provided to the instrument for use in treating tissue.

Where the term "approximately" is used herein in connection with a parameter having approximately a value, it is intended that the parameter can have exactly the value or can have another value which differs from the value due to environmental factors such as noise or due to hardware or software limitations such as, for example, number of bits, processor speed, or interrupt priority.

Figure 1:
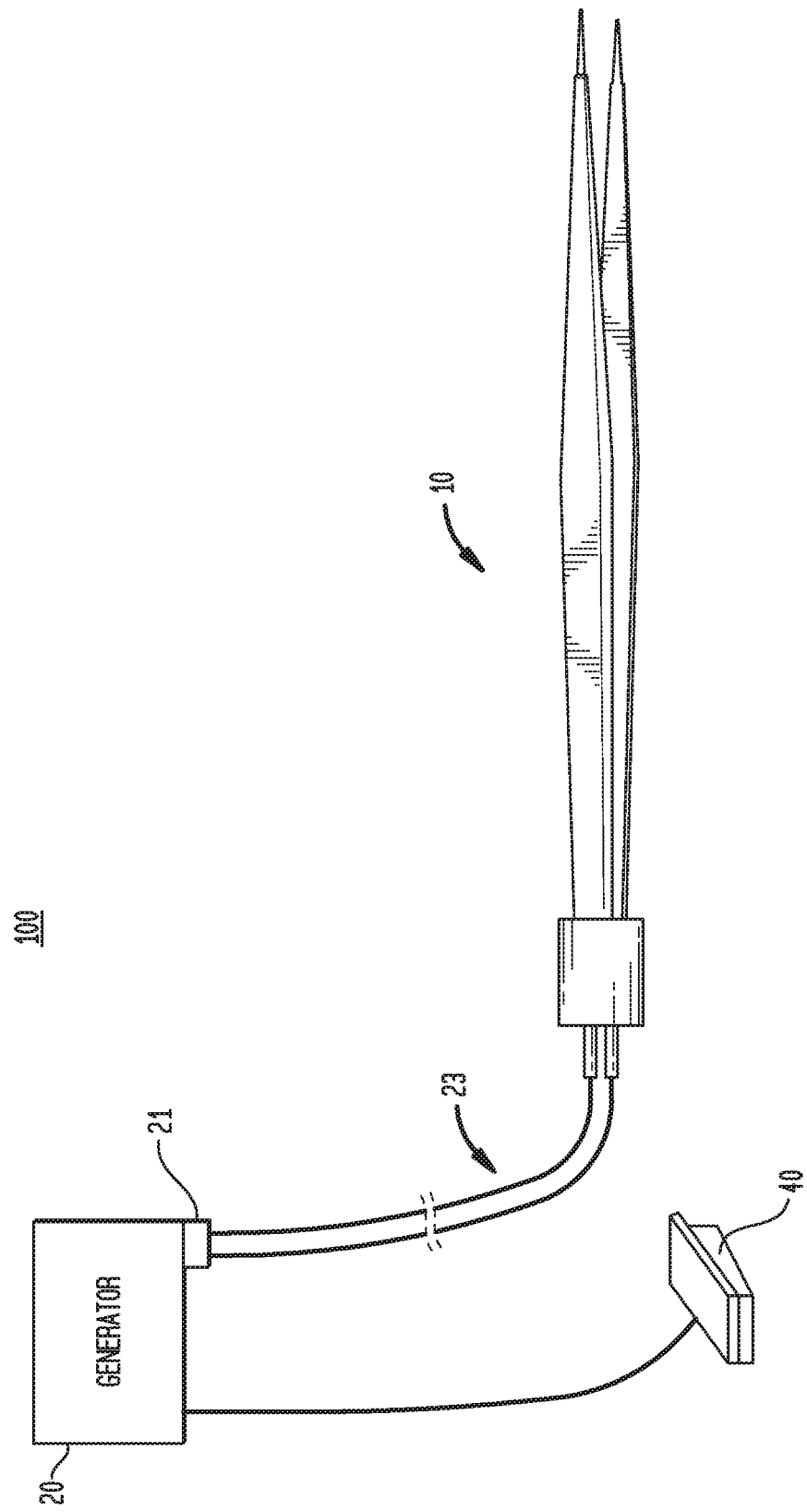
FIG. 1 is a schematic illustration, which shows an exemplary electrosurgical system including an electrosurgical generator in accordance with aspects of the present disclosure.

Referring now to FIG. 1, there is shown an illustration of an exemplary electrosurgical system 100 in accordance with aspects of the present disclosure. The system 100 includes an electrosurgical generator 20, an electrosurgical instrument 10, a cable 23 connecting the generator 20 and the instrument 10, and a foot switch 40. In various embodiments, the cable 23 and the instrument 10 may be separable. In various embodiments, the cable 23 may be attached to the instrument 10 and may be inseparable from the instrument 10. The generator 20 includes a port 21 that receives the cable 23. In various embodiments, the instrument 10 is a bipolar instrument and the port 21 of the generator 20 is a bipolar instrument port. As persons skilled in the art will recognize, a bipolar instrument receives electrical energy from a generator, applies a portion thereof to treat tissue through an active electrode, and returns a portion of the energy back to the generator through a return electrode. The instrument 10 illustrated in FIG. 1 is an exemplary bipolar forceps, which will be described in more detail in connection with FIG. 3. In various embodiments, the instrument 10 can be another type of electrosurgical instrument, such as a monopolar instrument with a return pad electrode, and the generator 20 can include one or more corresponding ports 21, such as monopolar ports.

With continuing reference to FIG. 1, the generator 20 includes a user interface (not shown) that enables a user to set the generator 20 to provide electrical energy for different types of procedures. In various embodiments, the generator 20 can provide electrical energy for vessel coagulation, tissue dissection, or other types of electrosurgical procedures. Persons skilled in the art will understand the electrosurgical parameters generally suitable for such procedures. In various embodiments, the user interface (not shown) can include an energy setting that permits a user to specify an electrical energy for the generator 20 to provide to the instrument 10.

When applying electrosurgical energy to dissect tissue, it is possible for tissue to become overly desiccated, thereby stalling the dissection process. Nevertheless, and in accordance with an aspect of the present disclosure, it has been found that by applying a controlled amount of extra energy (such as a power surge) at the initiation of a dissection process, while staying within regulatory guidelines for power accuracy, the ability to dissect tissue is improved. This process will be described in more detail in connection with FIG. 4.

In FIG. 1, the system 100 also includes a foot switch 40 that is in communication with the generator 20. The foot switch 40 can be depressed to indicate to the generator 20 that electrical energy should be activated and provided to the instrument 10, and release of the foot switch 40 can indicate to the generator 20 that electrical energy should be deactivated. The illustrated embodiment of FIG. 1 is exemplary, and configurations, components, and devices other than those illustrated are contemplated to be within the scope of the present disclosure.

Figure 2:
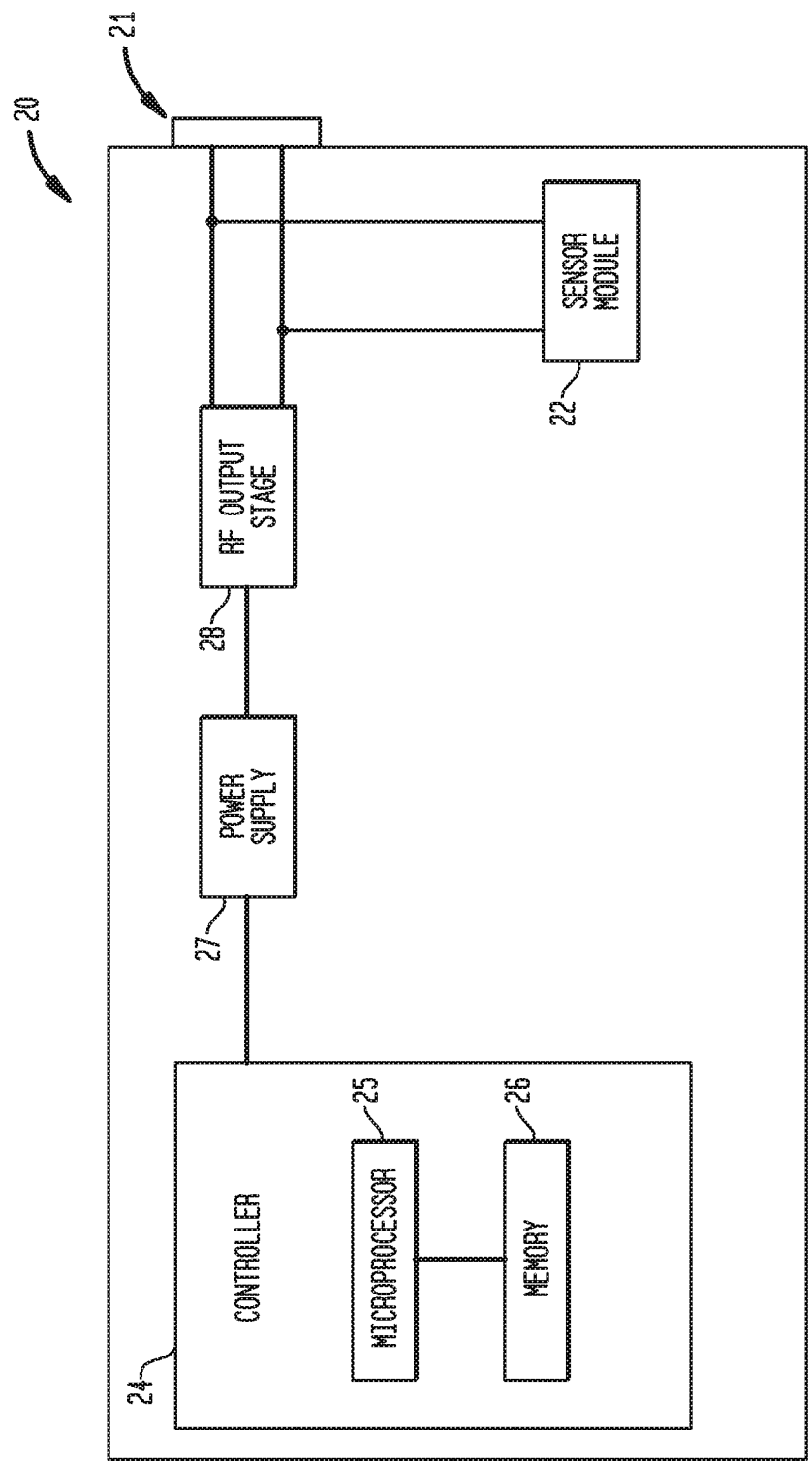
FIG. 2 shows a block diagram of exemplary components of the electrosurgical generator of FIG. 1 in accordance with aspects of the present disclosure.

Referring now to FIG. 2, there is shown a block diagram of exemplary components of an electrosurgical generator 20 in accordance with aspects of the present disclosure. In the illustrated embodiment, the generator 20 includes a controller 24, a power supply 27, a radio-frequency (RF) energy output stage 28, a sensor module 22, and one or more connector ports 21 that accommodate various types of electrosurgical instruments. The generator 20 can include a user interface (not shown), which permits a user to select various parameters for the generator 20, such as mode of operation and power setting. The mode of operation can include, for example, coagulation mode and tissue dissection mode. In various embodiments, the power setting can be specified by a user to be between zero and a power limit, such as, for example, five watts, thirty watts, seventy watts, or ninety-five watts.

In the illustrated embodiment, the controller 24 includes a microprocessor 25 and a memory 26. In various embodiments, the controller 24 or the microprocessor 25 may be another type of processor such as, without limitation, a digital signal processor, a field-programmable gate array (FPGA), or a central processing unit (CPU). In various embodiments, the memory 26 can be random access memory, read only memory, magnetic disk memory, solid state memory, optical disc memory, and/or another type of memory. In various embodiments, the memory 26 can be separate from the controller 24 and can communicate with the microprocessor 25 through communication buses of a circuit board and/or through communication cables such as serial ATA cables or other types of cables. The memory 26 includes machine instructions that are executable by the microprocessor 25 to operate the generator 20. Various operations of the generator 20 are described below. Such operations can be controlled by the machine instructions executed by the microprocessor 25.

With continuing reference to FIG. 2, in various embodiments, the power supply 27 can be a converter that receives AC energy, such as AC energy from a wall outlet, and converts the AC energy to DC energy. The power supply 27 can provide power to the controller 24 and can also be controllable by the controller 24. For example, the controller 24 can control the power supply 27 based on a user-specified power setting. The DC energy produced by the power supply 27 is conveyed to the RF energy output stage 28. In various embodiments, the RF output stage 28 converts the DC energy into an AC electrical waveform and conveys the waveform to an electrosurgical instrument through the connector port 21. In various embodiments, the RF output stage 28 can include an H-bridge that drives a resonant tank. Persons skilled in the art will understand the various implementations of the power supply 27 and the RF output stage 28, and will understand the AC electrical waveforms suitable for coagulation, tissue dissection, and other operations.

With continuing reference to FIG. 2, the sensor module 22 can include a voltage sensor and a current sensor, among other types of sensors. In various embodiments, the sensor module 22 and the controller 24 can cooperate to determine or estimate a load impedance of a load of the instrument. For example, the controller 24 can direct the RF output stage 28 to generate a non-therapeutic electrical waveform that can be used to determine or estimate a load impedance of a load of the instrument. The non-therapeutic electrical waveform corresponds to a voltage and current provided from the generator 20 to the instrument through the connector port 21 and corresponds to a return current that returns from the instrument to the generator 20 through the connector port 21. The return current can be sensed by the sensor module 22, which can communicate the return current measurements to the controller 24. The controller 24 can use the return current measurements to determine or estimate the load impedance of a load of the instrument. For example, the load impedance can be determined or estimated as the voltage provided by the RF output stage 28 divided by the sensed return current. In various embodiments, the voltage sensor of the sensor module 22 can sense the voltage provided to the connector port 21, and the sensed voltage can be used with the sensed return current to determine or estimate the load impedance of a load of the instrument. For example, the load impedance can be determined or estimated as the sensed voltage divided by the sensed return current. As will be described in more detail in connection with FIG. 4, if the load impedance is greater than a predetermined threshold, such as 8000 ohms, the controller 24 can determine that the instrument is not grasping tissue. On the other hand, if the load impedance is less than a predetermined threshold, such as four ohms, the controller 24 can determine that the active and return electrodes of the instrument are shorted together. Otherwise, the controller 24 can determine that the instrument is grasping tissue.

In various embodiments, the controller 24 and the sensor module 22 can determine whether the instrument is grasping tissue in other ways. As mentioned above, a user can set an energy setting at the generator 20, and the generator 20 can control the voltage and/or current provided by the power supply 27 and RF output stage 28 to provide the indicated energy. When the instrument is not grasping tissue, no meaningful current is drawn by the instrument. Thus, no treatment energy is actually provided by the generator 20 to the instrument, and the voltage at the output of the RF output stage 28 stays essentially the same. When the instrument grasps tissue, a current is then drawn by the instrument, which causes the generator 20 to vary the voltage to provide the indicated treatment energy setting. The variations in voltage can be characterized using a parameter known as crest factor, which persons skilled in the art will understand as a ratio of peak voltage to root-mean-squared (RMS) voltage. In various embodiments, the sensor module 22 can include one or more voltage sensors that measure voltages and can communicate the measurements to the controller 24 for the purpose of determining crest factor. In various embodiments, if the crest factor is greater than a predetermined threshold, the controller can determine that the instrument has grasped tissue. The illustrated embodiment of FIG. 2 is exemplary, and configurations, components, and devices other than those illustrated are contemplated to be within the scope of the present disclosure.

Figure 3:
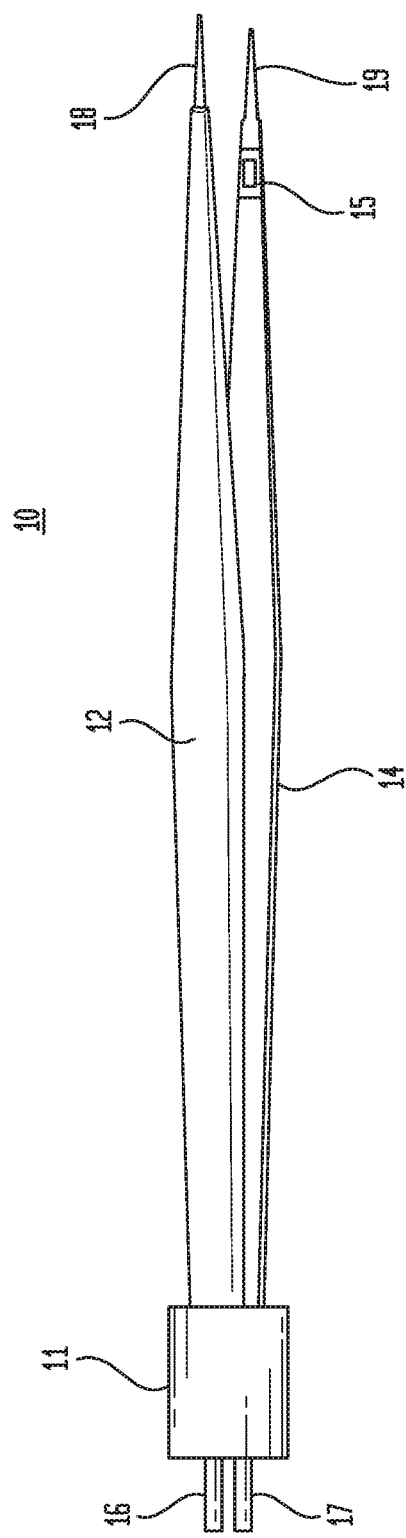
FIG. 3 shows a diagram of the electrosurgical instrument of FIG. 1.

FIG. 3 is an illustration of an exemplary instrument in accordance with aspects of the present disclosure. The instrument illustrated in FIG. 3 is a bipolar forceps 10, which may be used for various procedures such as vessel coagulation and tissue dissection. The bipolar forceps 10 includes an electrical connector 11 with two terminals 16, 17 configured to connect to an electrosurgical generator through a cable. One terminal 16 can convey current from the generator to the instrument 10, and the other terminal 17 can return current from the instrument 10 back to the generator.

The electrical connector 11 is attached to two arms 12, 14 that extend from the electrical connector 11. The two arms 12, 14 terminate in electrodes 18, 19 at the end opposite the electrical connector 11. One electrode 18 is referred to herein as an active electrode, and the other electrode 19 is referred to as a return electrode. The active electrode 18 conveys current received from the generator, and the return electrode 19 returns current back to the generator. The two arms 12, 14 include conductors (not shown) that connect the terminals 16, 17 of the electrical connector 11 with the electrodes 18, 19. Additionally, the two arms 12, 14 are mechanically biased away from each other so that the arms 12, 14 are apart in their resting state. A surgeon using the bipolar forceps 10 can squeeze the arms 12, 14 with varying amounts of force to press the arms 12, 14 and the electrodes 18, 19 closer together and to grasp tissue between the electrodes 18, 19.

In accordance with one aspect of the present disclosure, the instrument 10 can include one or more sensors 15 for determining whether the instrument 10 is grasping tissue. In connection with FIG. 3, the sensor 15 can be located on one or both of the arms 12, 14. In various embodiments, the sensor 15 can be a pressure sensor that indicates whether tissue is in contact with the pressure sensor. In various embodiments, the sensor 15 can be a light sensor that indicates whether tissue is occluding light from reaching the light sensor. The pressure sensor and/or the light sensor can be located in proximity to the active and return electrodes 18, 19, such that the sensor signals are indicative or whether the active and return electrodes 18, 19 are grasping tissue. In various embodiments, the sensor 15 can be arranged at another location of the instrument 10 as long as the sensor signals would be indicative of whether the active and return electrodes 18, 19 are grasping tissue. In various embodiments, the instrument 10 can include a manual switch (not shown) which a user can toggle to manually indicate whether tissue is grasped by the instrument 10. The signals from the pressure sensor, the light sensor, or the manual switch can be communicated from the instrument 10 to the generator. In various embodiments, the signals can be communicated using the terminals 16, 17 of the electrical connector 11. In various embodiments, the signals can be communicated using another conductor in the cable (FIG. 1, 23) connecting the instrument 10 and the generator, and the electrical connector 11 can include a third terminal (not shown) for this communication.

The illustrated embodiment of FIG. 3 is exemplary, and other instruments are contemplated to be within the scope of the present disclosure. In various embodiments, the instrument 10 can be another electrosurgical instrument that permits a surgeon to exert varying degrees of pressure on tissue by applying varying degrees of force to the instrument, such as Kleppinger forceps.

What have been described above are systems, methods, and devices for producing, controlling, and applying electrosurgical energy. The following will describe methods for controlling electrosurgical energy during a tissue dissection procedure.

In accordance with one aspect of the present disclosure, when tissue is grasped by an electrosurgical instrument and, for a predetermined length of time prior, no tissue had been grasped, a controlled energy surge can be provided to the instrument for use in dissecting tissue without overly desiccating the tissue. As mentioned above, when applying electrosurgical energy for dissecting tissue, it is possible for tissue to become overly desiccated, thereby stalling the dissection process. Overly desiccated tissue is likely to be difficult to dissect because the impedance of the tissue will be higher than normal. Nevertheless, and in accordance with an aspect of the present disclosure, it has been found that by applying a controlled amount of extra energy (i.e., power surge) at the initiation of a dissection process, while staying within regulatory guidelines for power accuracy, the ability to dissect tissue is improved without overly desiccating the tissue.

Figure 4:
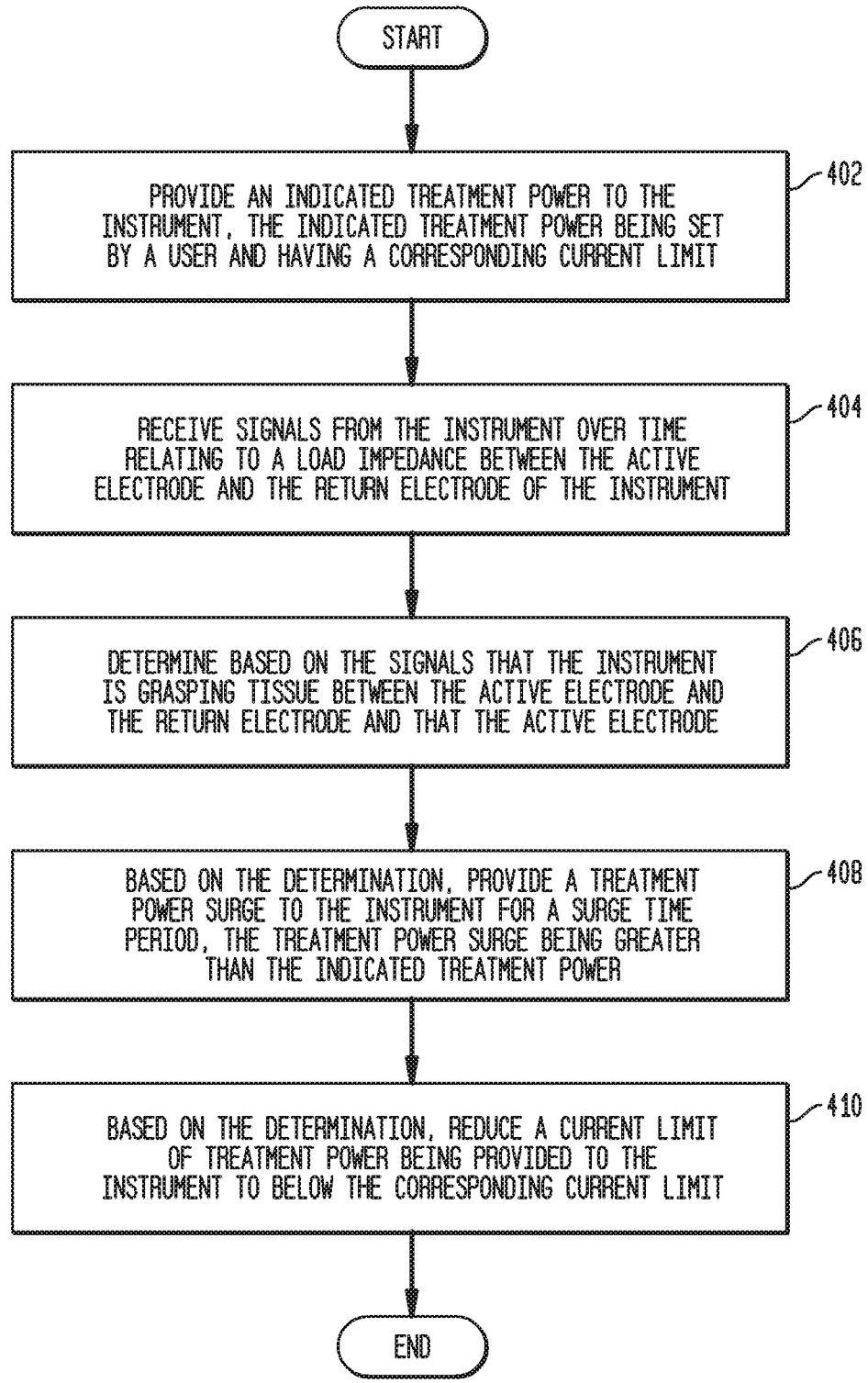
FIG. 4 shows a flow chart of an exemplary operation of an electrosurgical system in accordance with aspects of the present disclosure.

FIG. 4 shows a flow diagram of a method for a generator to provide a controlled power surge in accordance with aspects of the present disclosure. The disclosed method can be implemented in whole or in part by machine instructions stored in memory and executed on a processor. In various embodiments, the disclosed method can be implemented by a field-programmable gate array.

With reference also to FIG. 1, at step 402, the generator 20 can receive signals from the instrument 10 over time relating to whether tissue is grasped by the instrument. In various embodiments, as described above in connection with FIG. 2, the signals received by the generator 20 can be voltage and return current corresponding to a non-therapeutic electrical waveform, or the signals received by the generator 20 can be voltage signals for determining crest factor. In various embodiments, as described above in connection with FIG. 3, the signals received by the generator 20 can be signals of a pressure sensor, a light sensor, or a manual switch of the instrument 10. At step 404, the generator 20 can also receive an indication to provide an indicated treatment power to the instrument 10. As described above herein, the treatment power can be set by a user using a user interface of the generator 20.

At step 406, the signals received by the generator 20 can be used by the generator 20 to determine that tissue is grasped but that no tissue had been grasped for at least a predetermined amount of time. As described in connection with FIG. 2, load impedance or crest factor can be used to determine whether or not the instrument 10 is grasping tissue. Similarly, as described in connection with FIG. 3, signals of the pressure sensor, the light sensor, or the manual switch can be used to determine whether or not the instrument 10 is grasping tissue. In various embodiments, the controller (FIG. 2, 24) can use these signals over time to determine whether the instrument 10 has not grasped tissue for a predetermined length of time. In various embodiments, the predetermined length of time can be a length of time corresponding to a surgeon changing tissue treatment sites, such as approximately two seconds. In various embodiments, the predetermined length of time can correspond to a surgeon releasing and re-grasping the same tissue at a treatment site, such as approximately 0.5 seconds. In various embodiments, the predetermined length of time can correspond to an interval between two interrupts of the controller for determining whether tissue is grasped, such as an interval on the order of milliseconds.

At step 408, when the controller (FIG. 2, 24) determines that the instrument 10 is grasping tissue and that, for at least a predetermined length of time prior, no tissue had been grasped, the generator 20 provides a treatment power surge to the instrument 10 for a surge time period. The treatment power surge is greater than the treatment power indicated by the user power setting. In various embodiments, the treatment power surge can peak at one and half to four times the user power setting, and the surge time period can be two seconds or less. At step 410, after the surge time period, the generator 20 can provide the treatment power indicated by the power setting to the instrument 10.

Referring also to FIG. 2, the memory 26 can store various parameters for controlling the electrosurgical energy, such as power limit, voltage limit, current limit, ramp rate of power changes, ramp rate of voltage changes, and ramp rate of current changes, among other parameters. In various embodiments, these parameters are adjustable. In various embodiments, the power limit, the voltage limit, and the current limit are less than the maximum power, voltage, and current, respectively, that the generator 20 is capable of providing to the instrument.

In various embodiments, the treatment power surge can peak at one and half to four times the treatment power setting but cannot exceed a power limit, such as seventy watts or ninety-five Watts. In various embodiments, to reach the treatment power peak, the generator can increase the treatment power at a power change ramp rate, such as 325 Watts per second. In various embodiments, after the treatment power peaks, the generator can reduce the treatment power at a power change ramp rate, such as 325 Watts per second. In various embodiments, the power ramp-up rate and the power ramp-down rate may be different rates.

In various embodiments, the voltage limit can include a general voltage limit and a power surge voltage limit that is lower than the general voltage limit. For example, the voltage provided by the generator is controlled to not exceed the general voltage limit, or is lowered to the general voltage limit if the limit is exceeded. Additionally, during the power surge, the voltage provided by the generator is controlled to not exceed the power surge voltage limit, or is lowered to the power surge voltage limit if the limit is exceeded. In various embodiments, the voltage limit can include a power surge minimum voltage. For example, during the power surge, the voltage provided by the generator is controlled to not decrease below the power surge minimum voltage, or is increased to the power surge minimum voltage if the minimum is passed.

In various embodiments, the current limit can include a general current limit and a power surge current limit that is lower than the general current limit. For example, the current provided by the generator is controlled to not exceed the general current limit, or is lowered to the general current limit if the limit is exceeded. Additionally, during the power surge, the current provided by the generator is controlled to not exceed the power surge current limit, or is lowered to the power surge current limit if the limit is exceeded. In various embodiments, the current limit can include a power surge minimum current. For example, during the power surge, the current provided by the generator is controlled to not decrease below the power surge minimum current, or is increased to the power surge minimum current if the minimum is passed.

In various embodiments, when the controller 24 determines that no tissue is grasped, the controller 24 can control the power supply 27 and the RF output stage 28 to provide an output voltage at the voltage limit. When the controller 24 then determines that tissue is grasped, the controller 24 can control the power supply 27 and the RF output stage 28 to reduce the output voltage at a voltage change ramp rate.

Accordingly, what have been described are systems, methods, and devices for providing, controlling, and applying electrosurgical energy. Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. An electrosurgical generator for providing electrical treatment energy to an instrument, the generator comprising:
    a processor; and
    a memory having stored thereon instructions which, when executed by the processor, cause the generator to:
        receive signals from the instrument over time relating to whether tissue is grasped by the instrument, wherein the signals received from the instrument over time relating to whether tissue is grasped by the instrument include voltage signals for determining a crest factor for voltage provided by the generator;
        receive an indication to provide an indicated treatment power to the instrument, the indicated treatment power being set by a user;
        determine based on the signals that tissue is currently grasped and that, for at least a predetermined length of time prior, no tissue had been grasped, wherein the predetermined length of time corresponds to an interval between two interrupts of the processor for determining whether tissue is grasped;
        based on the determination, provide a treatment power surge to the instrument for a surge time period, the treatment power surge being greater than the indicated treatment power; and
        after the surge time period, provide the indicated treatment power to the instrument.

2. The electrosurgical generator of claim 1, wherein the signals received from the instrument over time include return current from the instrument to the generator, the generator further comprising a sensor configured to measure the return current.

3. The electrosurgical generator of claim 2, wherein the memory includes further instructions which, when executed by the processor, cause the generator to determine, based on the return current, a load impedance of a load of the instrument.

4. The electrosurgical generator of claim 3, wherein in determining that tissue is grasped, the memory includes further instructions which, when executed by the processor, cause the generator to determine that tissue is grasped based on the load impedance being lower than a load impedance threshold.

5. The electrosurgical generator of claim 3, wherein in determining that, for at least a predetermined length of time, no tissue had been grasped, the memory includes further instructions which, when executed by the processor, cause the generator to determine that no tissue had been grasped based on the load impedance being higher than a load impedance threshold for the predetermined length of time.

6. The electrosurgical generator of claim 1, wherein the treatment power surge peaks at 1.5 to 4 times the indicated treatment power.

7. The electrosurgical generator of claim 1, wherein the indicated treatment power set by the user is set for a tissue dissection mode of the generator, and wherein the instrument is a bipolar forceps that utilizes the indicated treatment power to dissect tissue.

8. A method in an electrosurgical generator for providing electrical treatment energy to an instrument, the method comprising:
    receiving signals from the instrument over time relating to whether tissue is grasped by the instrument, wherein the signals received from the instrument over time relating to whether tissue is grasped by the instrument include voltage signals for determining a crest factor for voltage provided by the generator;

receiving an indication to provide an indicated treatment power to the instrument, the indicated treatment power being set by a user;

determining based on the signals that tissue is currently grasped and that, for at least a predetermined length of time prior, no tissue had been grasped, wherein the predetermined length of time corresponds to an interval between two interrupts of the processor for determining whether tissue is grasped;

providing, based on the determining, a treatment power surge to the instrument for a surge time period, the treatment power surge being greater than the indicated treatment power; and providing, after the surge time period, the indicated treatment power to the instrument.

9. The method of claim 8, wherein receiving signals from the instrument over time includes receiving a return current from the instrument to the generator, the method further comprising measuring the return current.

10. The method of claim 9, further comprising determining, based on the return current, a load impedance of a load of the instrument.

11. The method of claim 10, wherein determining that tissue is grasped includes determining that tissue is grasped based on the load impedance being lower than a load impedance threshold.

12. The method of claim 10, wherein determining that, for at least a predetermined length of time, no tissue had been grasped, includes determining that no tissue had been grasped based on the load impedance being higher than a load impedance threshold for the predetermined length of time.

13. The method according to claim 8, wherein the treatment power surge peaks at 1.5 to 4 times the indicated treatment power.

14. The method according to claim 8, wherein the indicated treatment power set by the user is set for a tissue dissection mode of the generator, and wherein the instrument is a bipolar forceps that utilizes the indicated treatment power to dissect tissue.

15. A system for treating tissue, the system comprising:
an electrosurgical instrument configured to receive electrical treatment energy and to treat tissue; and
an electrosurgical generator including:
a processor; and
a memory having stored thereon instructions which, when executed by the processor, cause the generator to:
receive signals from the electrosurgical instrument over time relating to whether tissue is grasped by the electrosurgical instrument, wherein the signals received from the instrument over time relating to whether tissue is grasped by the instrument include voltage signals for determining a crest factor for voltage provided by the generator;
receive an indication to provide an indicated treatment power to the electrosurgical instrument, the indicated treatment power being set by a user;
determine based on the signals that tissue is currently grasped and that, for at least a predetermined length of time prior, no tissue had been grasped, wherein the predetermined length of time corresponds to an interval between two interrupts of the processor for determining whether tissue is grasped;
based on the determination, provide a treatment power surge to the electrosurgical instrument for a surge time period, the treatment power surge being greater than the indicated treatment power; and
after the surge time period, provide the indicated treatment power to the electrosurgical instrument.

\* \* \* \* \*